United States Patent [19]

Eskinazi

[11] 4,450,306

[45] May 22, 1984

[54] SELECTIVE CATALYTIC ALKYLATION OF PHENOLS TO ALKYL ARYL ETHERS

[75] Inventor: Victoria Eskinazi, Cleveland Heights, Ohio

[73] Assignee: Air Products and Chemicals, Inc., Allentown, Pa.

[21] Appl. No.: 440,133

[22] Filed: Nov. 8, 1982

[51] Int. Cl.³ ............................................. C07C 41/09
[52] U.S. Cl. .................... 568/630; 568/632; 568/658
[58] Field of Search ................. 568/630, 658, 632

[56] References Cited

U.S. PATENT DOCUMENTS

| | | | |
|---|---|---|---|
| 1,898,627 | 2/1933 | Hoffman et al. | 568/630 |
| 2,031,719 | 2/1936 | Langwell et al. | 568/658 X |
| 2,038,947 | 4/1936 | Maschmeijer et al. | 568/658 X |
| 2,477,091 | 7/1949 | Rosenwald | 568/658 X |
| 2,487,832 | 11/1949 | Searle | 568/630 |
| 3,446,856 | 5/1969 | Hamilton | 260/620 |
| 3,642,912 | 2/1972 | Sharp et al. | 260/621 |

FOREIGN PATENT DOCUMENTS 572300  3/1959  Canada ................................. 568/630

OTHER PUBLICATIONS

Jour. Amer. Chem. Soc., vol. 71, (1949), 1806–1816.
Thomke et al., Chem. Abs., vol. 78, (1973), 97028m.
Merck Index, Eighth Edition, 1968, p. 1226.

Primary Examiner—Bernard Helfin
Attorney, Agent, or Firm—Mark L. Rodgers; E. Eugene Innis; James C. Simmons

[57] ABSTRACT

$La_2(HPO_4)_3$, $Sr(HSO_4)_2$ and $Ba(HSO_4)_2$ are used, in either the gas or liquid phase, to catalyze the alkylation of phenols by alcohol to selectively form alkyl aryl ethers.

17 Claims, No Drawings

SELECTIVE CATALYTIC ALKYLATION OF PHENOLS TO ALKYL ARYL ETHERS

TECHNICAL FIELD OF THE INVENTION

The present invention relates to catalytic alkylation reactions. More particularly, it is concerned with the selective alkylation of phenols to yield alkyl aryl ethers.

BACKGROUND OF THE INVENTION

With the development of direct liquefaction of coal, and since phenolic compounds are a product of this direct liquefaction, the supply of phenols present in tar acids will increase to the point where the tar acids will present a disposal problem. One possible solution is using these phenols as fuel extenders. Because of the toxicity and corrosiveness of phenols, however, they must be converted to less hazardous compounds for most fuel applications. Major alternatives to the disposal of these phenolic tar acids are hydrotreating and conversion to methyl aryl ethers. The claimed invention provides a method for converting these phenols to alkyl aryl ethers which are good octane boosters and anti-knock agents.

The model reaction for the formation of methyl aryl ethers is the formation of anisole from phenol and methanol.

U.S. Pat. No. 2,487,832 teaches a process for preparing anisole by the alkylation of phenols using dimethylether and a solid dehydrating catalyst. An example of such a solid dehydrating catalyst is alumina. Although alumina is a good catalyst for phenol alkylation, it has some selectivity for c-alkylation, producing cresols which are as toxic and corrosive as the phenols and therefore is not a suitable catalyst for phenol alkylation.

Another solid dehydrating catalyst, thoria, is also described in this patent. Thoria is highly selective for O-alkylation of phenol but its radioactivity makes it an unattractive alternative to other catalysts.

U.S. Pat. No. 3,642,912 also discloses a process for the catalytic alkylation of phenols. The catalysts described in this patent are titanium dioxide and derivatives thereof. These catalysts also prove to be good alkylating agents of phenols but, as with alumina, some selectivity to c-alkylation takes place producing unwanted cresols.

Anisole can also be selectively synthesized from sodium phenoxide and dimethylsulfate in the presence of NaOH. This process is known as the Williamson synthesis; see the Merck Index, Eighth Edition, 1968, page 1226. Because stoichiometric quantities of sodium hydroxide are required to produce the sodium phenoxide and because of the large quantities of salt by-product however, this type of process has little commercial appeal.

SUMMARY OF THE INVENTION

It has now been found that alkylation of phenols with alcohols when carried out using $La_2(HPO_4)_3$, $Sr(HSO_4)_2$ or $Ba(HSO_4)_2$ catalysts in either the gas or liquid phase can result in high alkyl aryl ether selectivity with little cresol formation.

DETAILED DESCRIPTION OF THE INVENTION

The present invention consists of a process for etherification of phenols and alcohols to alkyl aryl ethers using $La_2(HPO_4)_3$ $Ba(HSO_4)_2$ or $Sr(HSO_4)_2$ catalysts.

The catalysts disclosed in the presently claimed process, have up to 99% selectivity for O-alkylation resulting in the production of alkyl aryl ethers, with very little cresol formation. The claimed process can be carried out using these catalysts in either the gas phase or liquid phase.

The preferred temperature range of operation of this process is from 250° C. to 350° C. Above 350° C. selectivity to O-alkylation decreases. In a liquid phase operation the preferred reaction time is in the range of about 3-5 hours. Longer reaction times give higher conversion, but lower alkyl aryl ether selectivity. It is also preferred to run this reaction with alcohol in excess.

The phenol feed used in the claimed reaction can include phenol, cresols, xylenols, naphthols, the substituted phenols found in coal liquids, and crude coal liquids. While any alcohol can be used which is capable of alkylating the particular phenol feed used, only C-1 to C-12 alcohols have practical application with C-1 to C-4 alcohols being preferred.

The reaction product is an alkyl aryl ether generally having the structural formula R—O—R' wherein R is the monovalent radical of phenol, cresol, xylenol, naphthol or the substituted phenols found in coal liquids and R' is any C-1 to C-12 aliphatic hydrocarbyl group. A hydrocarbyl group is defined as the monovalent radical of any hydrocarbon.

When carried out in the gas phase, this process can be operated at a pressure range of about 0 to 1200 psig, with 0 to 100 psig being preferred, and at a gas hourly space velocity (GHSV) of the phenolic feed stock per volume of catalyst in the range of about 500 to 700. An inert carrier gas such as nitrogen, argon or helium may also be used but is not required.

When carried out in a stirred reactor in the liquid phase, the reaction can be carried out at a considerably higher pressure range. This pressure range is anywhere between about 0 to 2000 psig, with 500 to 1200 psig being preferred.

Producing methyl aryl ethers using the type of catalyst of the present invention under the conditions applied is superior to the processes of the prior art which use alkali metal phenoxides because there is not the problem of disposal of inorganic salts nor the cost of alkali metal hydroxides. This method is also superior to previous applications of heterogeneous catalysts other than thoria because selectivity to anisole is higher. It is also superior to the use of thoria because it does not involve radioactive materials. The use of catalysts of this invention provides reduced toxicity in the process.

When phenol and methanol are used in the claimed process, the catalyst system also has the advantage of minimizing the extent of isomerization of anisole, once formed, to cresols.

The $La_2(HPO_4)_3$ catalyst is prepared by mixing an aqueous solution of $La(NO_3)_3$ with a solution of $(NH_4)_2HPO_4$. The mixture is stirred and $La_2(HPO_4)_3$ precipitates out.

The $Ba(HSO_4)_2$ and $Sr(HSO_4)_2$ catalysts are prepared by mixing aqueous solutions of $Ba(NO_3)_2$ and $Sr(NO_3)_2$ respectively with $NH_4HSO_4$ and stirring the mixture. The desired catalysts precipitate out of the solution.

CATALYST PREPARATION

EXAMPLE 1

The $La_2(HPO_4)_3$ catalyst was prepared by mixing together a 2.0 M aqueous solution of $La(NO_3)_3.5H_2O$ (415 g, dilute with H$_2$O to 500 cc) and a 3.00 M solution of (NH$_4$)$_2$HPO$_4$ (198 g, dilute with H$_2$O to 500 cc). The mixture was stirred a few minutes and the La$_2$(HPO$_4$)$_3$ precipitate filtered, washed and dried. In this catalyst preparation it is inherent that some La$_2$(PO$_4$)$_3$ will also be found.

EXAMPLE 2

The Ba(HSO$_4$)$_2$ catalyst, was prepared as above using a 2.0 M solution of Ba(NO$_3$)$_2$ (261 g, dilute with H$_2$O to 500 cc) and 4.0 M solution of NH$_4$HSO$_4$ (230 g, dilute with H$_2$O to 500 cc).

EXAMPLE 3

The Sr(HSO$_4$)$_2$ catalyst was prepared as above using a 2.0 M solution of Sr(NO$_3$)$_2$ (212 g, dilute with H$_2$O to 500 cc) and a 4.0 M solution of NH$_4$HSO$_4$ (230 g, dilute with H$_2$O to 500 cc).

USE OF CATALYSTS

The following are examples of etherification reactions in which the above catalysts were employed. These examples are meant to be illustrative and not limiting.

EXAMPLE 4

8.65 g (5 cc) of La$_2$(HPO$_4$)$_3$ was loosely packed as a fixed bed in a vertical down-flow tube reactor (inside diameter=1.1 cm). The system was purged with helium and heated to 300° C. A feed of phenol, methanol, and helium in molar ratios of 14.1:70.6:15.3 at 1 psig was passed over the catalyst with GHSV=538. The resulting product was trapped at approximately −25° C. and the liquid analyzed for phenol derivatives. The components of the stripped exit gas were also analyzed. The results of the analysis of both the liquid and the exit gas are reported in Table 1.

TABLE 1

| Exit Gas Rate: 521 SCCH | | Liquid Recovered: 4.45 g/hr | |
|---|---|---|---|
| Component | Mole % | Component | Wt. % |
| MeOH | trace | Anisole | 5.33 |
| H$_2$O | trace | o-Cresol | 0.257 |
| CH$_3$OCH$_3$ | 5.66 | m,p-Cresol | 0.053 |
| H$_2$ | — | Methylanisoles | — |
| CO$_2$ | 0.13 | Other aromatics | 0.019 |
| CH$_4$ | trace | | |
| C$_2$H$_4$ | trace | | |
| C$_2$H$_6$ | — | | |

As shown in Table 1, the liquid product contained 5.33% anisole, 0.257% o-cresol and 0.053% meta and para cresol with a selectivity of 94.2% to anisole.

EXAMPLE 5

La$_2$(HPO$_4$)$_3$ was tested in the same system used in Example 4 at 401° C. A feed of phenol, methanol, and helium in molar ratios of 14.1:70.5:15.3 at 1 psig was passed over the catalyst with a GHSV=652. The analytical results of this test are shown in Table 2.

TABLE 2

| Exit Gas Rate: 652 SCCH | | Liquid Recovered: 4.75 g/hr | |
|---|---|---|---|
| Component | Mole % | Component | Wt. % |
| MeOH | — | Anisole | 20.5 |
| H$_2$O | trace | o-Cresol | 5.10 |
| CH$_3$OCH$_3$ | 9.4 | m,p-Cresol | 1.88 |
| H$_2$ | — | Methylanisoles | 4.36 |
| CO | — | Dimethylphenols | 2.15 |
| CO$_2$ | 0.092 | Other aromatics | 1.08 |
| CH$_4$ | 25.7 | | |
| C$_2$H$_4$ | 0.55 | | |
| C$_2$H$_6$ | 0.53 | | |

The product contained 20.5% anisole, 5.10% o-cresol and 9.47% other alkylation products. The selectivity was 57.2% to anisole.

EXAMPLE 6

La$_2$(HPO$_4$)$_3$ was tested in the same system used in Example 4 at 349° C. A feed of phenol, methanol, and helium in molar ratios of 14.1:70.6:15.2 was passed over the catalyst with a GHSV=657. The results of this analysis are contained in Table 3.

TABLE 3

| Exit Gas Rate: 657 SCCH | | Liquid Recovered: 4.91 g/hr | |
|---|---|---|---|
| Component | Mole % | Component | Wt. % |
| MeOH | — | Anisole | 15.7 |
| H$_2$O | trace | o-Cresol | 1.94 |
| CH$_3$OCH$_3$ | 7.89 | m,p-Cresol | 0.58 |
| H$_2$ | — | Methylanisoles | 0.84 |
| CO | — | Dimethylphenols | 0.28 |
| CO$_2$ | trace | Other aromatics | 0.09 |
| CH$_4$ | 4.0 | | |
| C$_2$H$_4$ | trace | | |
| C$_2$H$_6$ | trace | | |

The selectivity was 81% to anisole.

EXAMPLE 7

This example shows that the reaction can be conducted in a stirred reactor in the liquid phase. 5.0 g of La$_2$(HPO$_4$)$_3$ was loaded into a stirred 300 ml reactor with 50 g of a 37 wt.% phenol in methanol solution. The reactor was purged with helium at 1 atmosphere and sealed. The temperature was increased to 300° C., which pressurizes the system to 1200 psig, and the reactor operated at 1,000 RPM. After 4 hours the reactor was cooled and a sample taken. The results of this reaction are reported in Table 4.

TABLE 4

| Liquid Product | wt % @ 4hr. | wt % @ 19hr. |
|---|---|---|
| Anisole | 20.6 | 31.2 |
| o-cresol | 0.50 | 2.07 |
| m,p-cresol | 0.08 | 0.35 |
| methylanisoles | 0.14 | 1.22 |
| dimethylphenols | 0.005 | 0.38 |
| other aromatics | 0.03 | 1.03 |
| Conversion | 50.2% | 85.3% |
| Selectivity | 96.6% | 86.% |

This table shows that, while reactant conversion increases with time, selectivity for the desired product decreases.

EXAMPLE 8

Liquid phase alkylation was also conducted as in Example 4 using 75% phenol in methanol, with the system pressurized to 600 psig and run for 4 hours. The results of this run are shown in Table 5.

TABLE 5

| Liquid Product | wt % @ 4hr. |
|---|---|
| Anisole | 38.0 |
| o-cresol | 0.27 |
| m,p-cresol | 0.02 |
| methylanisoles | 0.0258 |
| dimethylphenol | 0.03 |
| other aromatics | 0.09 |
| Conversion | 45.0% |
| Selectivity | 99.0% |

EXAMPLE 9

6.44 g (5 cc) of $Sr(HSO_4)_2$ was tested in the system described in Example 4 at 299° C. A feed of phenol, methanol and helium was passed over the catalyst in molar ratios of 14.3:71.5:14.2 at GHSV=633. The results of this test are shown in Table 6.

TABLE 6

| Exit Gas Rate: 447 SCCH | | Liquid Recovered: 5.02 g/hr | |
|---|---|---|---|
| Component | Mole % | Component | Wt. % |
| MeOH | — | Anisole | 0.2 |
| $H_2O$ | trace | o-Cresol | 0.05 |
| $CH_3OCH_3$ | trace | m,p-Cresol | — |
| $H_2$ | — | Methylanisoles | — |
| CO | — | Dimethylphenols | — |
| $CO_2$ | trace | Other aromatics | — |
| $CH_4$ | trace | | |
| $C_2H_4$ | — | | |
| $C_2H_6$ | — | | |

The selectivity to anisole was about 80% with a yield of 0.0016 g anisole/g catalyst hour.

EXAMPLE 10

6.86 g (5.0 cc) of $Ba(HSO_4)_2$ was tested in the system described in Example 4 at 300° C. A feed of phenol, methanol and helium in molar ratios of 14.2:70.8:15.0 was passed over the catalyst at GHSV=599. The results of this test are shown in Table 7.

TABLE 7

| Exit Gas Rate: 453 SCCH | | Liquid Recovered: 4.68 g/hr | |
|---|---|---|---|
| Component | Mole % | Component | Wt. % |
| MeOH | 0.85 | Anisole | 2.95 |
| $H_2O$ | 0.30 | o-Cresol | 0.237 |
| $CH_3OCH_3$ | 3.22 | m,p-Cresol | 0.050 |
| $H_2$ | — | Methylanisoles | — |
| CO | — | Dimethylphenols | — |
| $CO_2$ | — | Other aromatics | — |
| $CH_4$ | trace | | |
| $C_2H_4$ | — | | |
| $C_2H_6$ | — | | |

The selectivity was 91.1% to anisole with a yield of 0.20 g anisole/g catalyst hour.

Control 1

For a comparison, 9.23 g (10 cc) of Alcoa alumina F/20 was tested in the system described in Example 4 at 303° C. Alumina is an acidic catalyst which will promote alkylation of aromatics. A feed of phenol, methanol and helium was passed over the catalyst in molar ratios of 13.8:68.9:17.3 at GHSV=521. The results of this test are shown in Table 8.

TABLE 8

| Exit Gas Rate: 1038 SCCH | | Liquid Recovered: 7.73 g/hr | |
|---|---|---|---|
| Component | Mole % | Component | Wt. % |
| MeOH | — | Anisole | 8.2 |
| $H_2O$ | trace | o-Cresol | 1.8 |
| $CH_3OCH_3$ | 2.31 | m,p-Cresol | 0.092 |
| $H_2$ | — | Methylanisoles | 0.060 |
| CO | — | Dimethylphenols | — |
| $CO_2$ | trace | Other aromatics | 0.60 |
| $CH_4$ | — | | |
| $C_2H_4$ | — | | |
| $C_2H_6$ | — | | |

The selectivity to anisole was 76.3% with a yield of 0.069 g anisole/g catalyst hour. Although this catalyst resulted in good selectivity to anisole, it also resulted in a 16.7% selectivity for cresol. It is this relatively large cresol formation which demonstrates the need for the type of catalysts defined in this invention.

Control 2

Also for comparison 5.60 g (10 cc) of synthetic zeolite catalyst HZSM5 was tested in the system described in Example 4 at 299° C. A feed of phenol, methanol and helium was passed over the catalyst in molar ratios of 13.9:69.5:16.7 at GHSV=540. The results of this test are shown in Table 9.

TABLE 9

| Exit Gas Rate: 1000 SCCH | | Liquid Recovered: 7.71 g/hr | |
|---|---|---|---|
| Component | Mole % | Component | Wt. % |
| MeOH | 0.82 | Anisole | 6.0 |
| $H_2O$ | trace | o-Cresol | 2.4 |
| $CH_3OCH_3$ | 11.8 | m,p-Cresol | 1.4 |
| $H_2O$ | 0.24 | Methylanisoles | 0.20 |
| CO | 0.15 | Dimethylphenols | 0.24 |
| $CO_2$ | — | Other aromatics | 0.16 |
| $CH_4$ | 0.34 | | |
| $C_2H_4$ | 0.86 | | |
| $C_2H_6$ | 0.057 | | |

The selectivity to anisole was 57.7% with a yield of 0.083 g anisole/g catalyst hour. This poor selectivity also demonstrates the need for the catalyst defined in this invention.

What is claimed is:

1. In a method for the alkylation of phenols by alcohols to yield alkyl aryl ethers, the improvement which comprises the use of $Sr(HSO_4)_2$ or $Ba(HSO_4)_2$ catalysts or mixtures thereof.

2. A method according to claim 1 wherein said reaction is carried out between 250° C.–350° C.

3. A method according to claim 1 wherein said catalysts are in the gas phase.

4. A method according to claim 1 wherein said catalysts are in the liquid phase.

5. A method according to claim 1 wherein said alcohol is a C-1 to C-4 alcohol.

6. A method according to claim 1 wherein said alkyl aryl ether is anisole.

7. A method according to claim 1 wherein said phenols are the substituted phenols found in coal liquids.

8. In a method for the alkylation of phenols by alcohols to yield alkyl aryl ethers having the structural formula R—O—R', where R is the monovalent radical of phenol, cresol, xylenol, naphthol or the substituted phenols found in coal liquids and R' is any C-1 to C-12 aliphatic hydrocarbyl group, the improvement which comprises the use of $Sr(HSO_4)_2$ or $Ba(HSO_4)_2$ catalysts or mixtures thereof.

9. A method according to claim 2 wherein said reaction is carried out between 250° C.–350° C.

10. A method according to claim 2 wherein said catalysts are in the gas phase.

11. A method according to claim 2 wherein said catalysts are in the liquid phase.

12. A method according to claim 2 wherein said alcohol is a C-1 to C-4 alcohol.

13. A method according to claim 2 wherein said alkyl aryl ether is anisole.

14. A method according to claim 2 wherein said phenols are the substituted phenols found in coal liquids.

15. A method for alkylating phenol with methanol to yield anisole, comprising using $Sr(HSO_4)_2$ or $Ba(HSO_4)_2$ catalysts or a mixture thereof in the gas phase, at a temperature in the range of about 250° C. to 350° C. and pressure in the range of about 0 to 100 psig.

16. A method according to claim 15 wherein an inert carrier gas is added.

17. A method for alkylating phenol with methanol to yield anisole, comprising using $Sr(HSO_4)_2$ or $Ba(HSO_4)_2$ catalysts or a mixture thereof in the liquid phase at a temperature in the range of about 250° C. to 350° C. and pressure in the range of about 500 to 1200 psig.

* * * * *

UNITED STATES PATENT AND TRADEMARK OFFICE
CERTIFICATE OF CORRECTION

PATENT NO. : 4,450,306
DATED : May 22, 1984
INVENTOR(S) : Victoria Eskinazi

It is certified that error appears in the above-identified patent and that said Letters Patent are hereby corrected as shown below:

Column 7, Line 4
   Delete "2" and substitute therefor -- 8 --

Column 7, Line 6
   Delete "2" and substitute therefor -- 8 --

Column 7, Line 9
   Delete "2" and substitute therefor -- 8 --

Column 7, Line 11
   Delete "2" and substitute therefor -- 8 --

Column 7, Line 14
   Delete "2" and substitute therefor -- 8 --

Signed and Sealed this

Eleventh Day of June 1985

[SEAL]

Attest:

DONALD J. QUIGG

Attesting Officer

Acting Commissioner of Patents and Trademarks